United States Patent
Bauss et al.

(10) Patent No.: US 11,195,604 B2
(45) Date of Patent: *Dec. 7, 2021

(54) MEDICAMENT DELIVERY DEVICE

(71) Applicant: SHL Medical AG, Zug (SE)

(72) Inventors: Markus Bauss, Lengdorf (DE); Per Lindstedt, Varmdo (SE); Rasmus Renstad, Stockholm (SE); Nikolaj Hautaviita, Bro (SE); Daniel Sall, Segeltorp (SE)

(73) Assignee: SHL Medical AG, Zug (CH)

( * ) Notice: Subject to any disclaimer, the term of this patent is extended or adjusted under 35 U.S.C. 154(b) by 373 days.

This patent is subject to a terminal disclaimer.

(21) Appl. No.: 16/534,342

(22) Filed: Aug. 7, 2019

(65) Prior Publication Data

US 2020/0030535 A1 Jan. 30, 2020

Related U.S. Application Data

(63) Continuation of application No. 15/517,294, filed as application No. PCT/EP2015/072410 on Sep. 29, 2015, now Pat. No. 10,391,247.

(Continued)

(30) Foreign Application Priority Data

Feb. 23, 2015 (EP) ..................................... 15156116

(51) Int. Cl.
*A61M 5/20* (2006.01)
*A61M 5/315* (2006.01)
(Continued)

(52) U.S. Cl.
CPC .......... *G16H 20/13* (2018.01); *A61M 5/2033* (2013.01); *A61M 5/3157* (2013.01);
(Continued)

(58) Field of Classification Search
CPC ............ A61M 2005/2013; A61M 5/20; A61M 2005/202; A61M 2205/3569;
(Continued)

(56) References Cited

U.S. PATENT DOCUMENTS 8,355,753 B2   1/2013 Bochenko et al.
10,391,247 B2 * 8/2019 Bauss .................... G09B 5/065
(Continued)

FOREIGN PATENT DOCUMENTS

EP       2243460 A1    10/2010
TW     201212888 A      4/2012
(Continued)

OTHER PUBLICATIONS

European Search Report for EP Application No. EP 19173236, dated Aug. 9, 2019.
(Continued)

*Primary Examiner* — Quynh-Nhu H. Vu
(74) *Attorney, Agent, or Firm* — McDonnell Boehnen Hulbert & Berghoff LLP

(57) ABSTRACT

The present invention relates to a medicament delivery device comprising a housing (60), which housing is arranged to accommodate a medicament container (62); a drive unit (86) operably arranged to act on said medicament container (62) for expelling a dose of medicament; an activation unit (74) operably connected to said drive unit for activating said drive unit (86); said drive unit (86) comprising an actuation element (84) arranged movable inside the housing (60) from an initial position prior to activation, to a displaced position after activation; at least a first NFC-chip (170, 172) comprising specific information arranged on said actuation element; at least one shielding element (174) arranged to said housing, such as to shield said at least first NFC-chip (170, 172) from being read by an NFC-chip (Continued)

reader when said actuation element (84) is either in the initial position or in the displaced position. The present invention also comprises a communication system in which said medicament delivery device is a part.

20 Claims, 12 Drawing Sheets

Related U.S. Application Data

(60) Provisional application No. 62/060,276, filed on Oct. 6, 2014.

(51) Int. Cl.

| | | |
|---|---|---|
| *A61M 15/00* | (2006.01) | |
| *G16H 20/17* | (2018.01) | |
| *G16H 20/10* | (2018.01) | |
| *G16H 20/13* | (2018.01) | |
| *G16H 40/63* | (2018.01) | |
| *G09B 1/14* | (2006.01) | |
| *G09B 1/32* | (2006.01) | |
| *G09B 5/06* | (2006.01) | |
| *G16H 10/20* | (2018.01) | |

(52) U.S. Cl.
CPC ............... *A61M 15/00* (2013.01); *G09B 1/14* (2013.01); *G09B 1/325* (2013.01); *G09B 5/062* (2013.01); *G09B 5/065* (2013.01); *G16H 20/10* (2018.01); *G16H 20/17* (2018.01); *G16H 40/63* (2018.01); *A61M 2005/202* (2013.01); *A61M 2005/2013* (2013.01); *A61M 2205/3569* (2013.01); *A61M 2205/3584* (2013.01); *A61M 2205/581* (2013.01); *A61M 2205/582* (2013.01); *A61M 2205/583* (2013.01); *A61M 2205/60* (2013.01); *A61M 2205/6009* (2013.01); *A61M 2205/609* (2013.01); *A61M 2205/6054* (2013.01); *G16H 10/20* (2018.01)

(58) Field of Classification Search
CPC .... A61M 2205/3584; A61M 2205/581; A61M 2205/582; A61M 2205/583; A61M 2205/60; A61M 2205/6009; A61M 2205/6054; A61M 2205/609; A61M 5/2033; A61M 2205/3576; A61M 5/3157; G16H 10/20; G16H 20/10; G16H 20/13; G16H 20/17; G16H 40/63; G09B 1/14; G09B 1/325; G09B 5/062; G09B 5/065
See application file for complete search history.

(56) References Cited

U.S. PATENT DOCUMENTS

| | | |
|---|---|---|
| 2002/0096543 A1 | 7/2002 | Juselius |
| 2004/0178112 A1 | 9/2004 | Snyder |
| 2005/0182358 A1 | 8/2005 | Veit et al. |
| 2006/0169773 A1 | 8/2006 | Lyons et al. |
| 2007/0129708 A1 | 6/2007 | Edwards et al. |
| 2007/0274242 A1* | 11/2007 | Lamacraft .......... G06K 19/0723 370/310 |
| 2011/0111794 A1 | 5/2011 | Bochenko et al. |
| 2011/0231204 A1 | 9/2011 | De La Huerga |
| 2012/0326885 A1 | 12/2012 | McCarty |
| 2013/0046197 A1 | 2/2013 | Dlugos, Jr. et al. |
| 2013/0181814 A1* | 7/2013 | Smith .............. G06K 19/07327 340/10.1 |
| 2013/0184649 A1* | 7/2013 | Edwards ............ A61M 5/2448 604/195 |
| 2013/0285681 A1 | 10/2013 | Wilson et al. |
| 2014/0292493 A1 | 10/2014 | Clarke et al. |
| 2014/0312074 A1 | 10/2014 | Madsen et al. |
| 2015/0025498 A1 | 1/2015 | Estes |

FOREIGN PATENT DOCUMENTS

| | | |
|---|---|---|
| TW | 201406420 A | 2/2014 |
| WO | 2004/023245 A2 | 3/2004 |
| WO | 2004084116 A1 | 9/2004 |
| WO | 2006/083933 A1 | 8/2006 |
| WO | 2012/108938 A1 | 8/2012 |
| WO | 2013/167701 A1 | 11/2013 |

OTHER PUBLICATIONS

English Translation of Search Report issued in Taiwanese Patent Application No. 104132583 dated Feb. 23, 2016.
International Search Report issued in International Application No. PCT/EP2015/072410 dated Mar. 7, 2016.
Search Report issued in European Patent Application No. 1515116 dated Apr. 8, 2016.

* cited by examiner

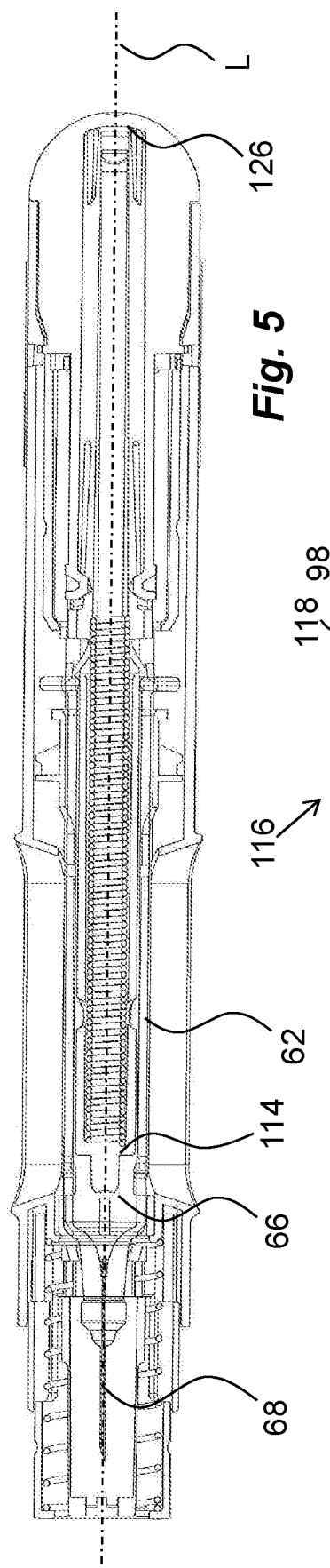
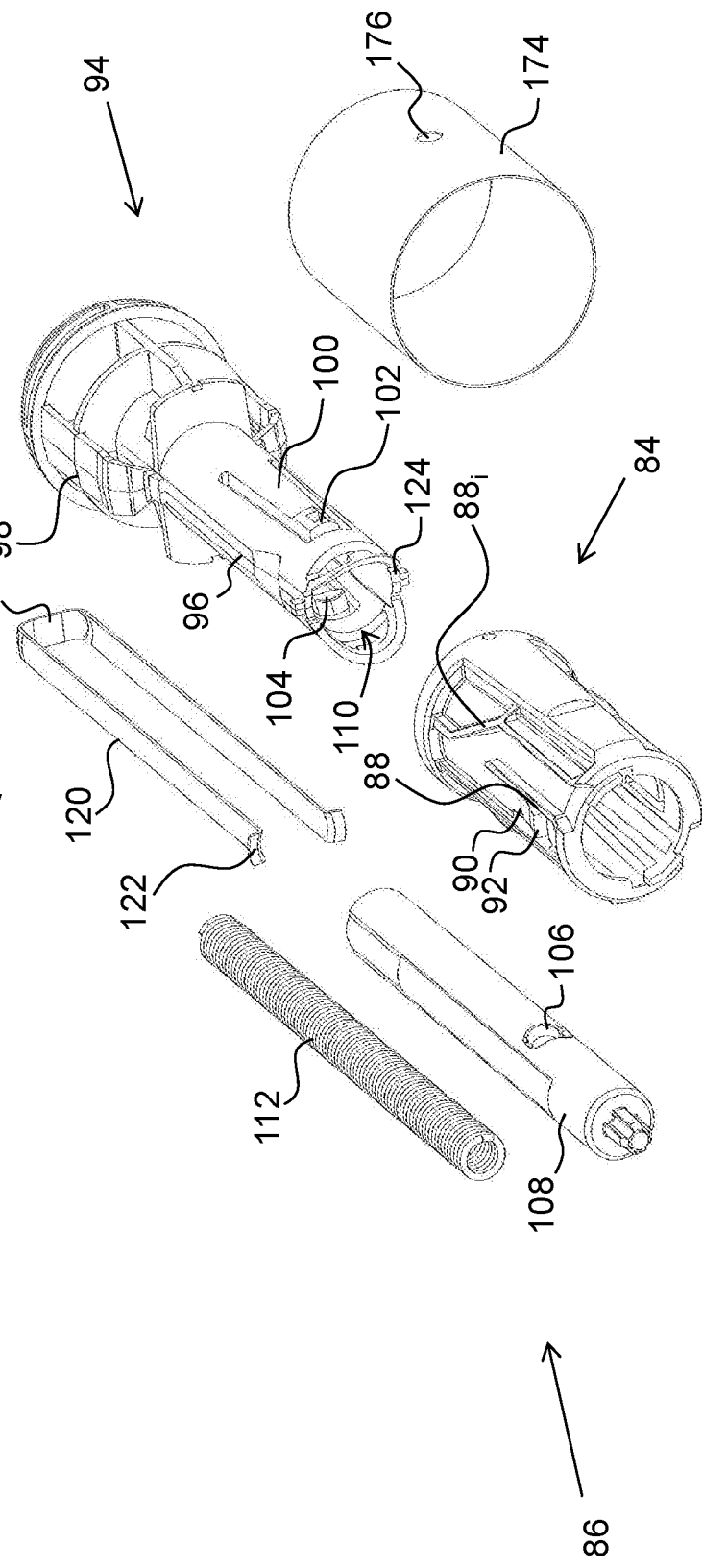
Fig. 5
Fig. 6

MEDICAMENT DELIVERY DEVICE

CROSS REFERENCE TO RELATED APPLICATIONS

The present application is a Continuation of U.S. patent application Ser. No. 15/517,294 filed Apr. 6, 2017, which is a U.S. National Phase Application pursuant to 35 U.S.C. § 371 of International Application No. PCT/EP2015/072410 filed Sep. 29, 2015, which claims which claims the benefit of U.S. Provisional Patent Application No. 62/060,276, filed Oct. 6, 2014, which claims priority to European Patent Application No. 15156116.4, filed Feb. 23, 2015. The entire disclosure contents of these applications are herewith incorporated by reference into the present application.

TECHNICAL AREA

The present invention relates to a medicament delivery device as well as a communication system comprising the medicament delivery device and in particular a communication system related to administration of drugs to users.

BACKGROUND OF INVENTION

Medicament delivery devices for self-administration have been on the market for a number of years. In order for the devices to be handled by non-professionals, they have to be easy to use and intuitive. Further, since many of the drugs are vital or at least very important to the patient there is a desire from physicians and other professionals to obtain information that the patients medicate according to prescribed schemes. The desired information could include the type of drug, delivery times and dates, dose size. Additional information that could be beneficial to the physician is that the drug has being taken using the correct procedure according to instructions for use; that the drug has the prescribed temperature during drug delivery; that the right injection depth has been used and that the correct injection speed has been used, when the medicament delivery device is an injector.

In order to obtain this information from the medicament delivery device, a number of solutions have been presented. Document WO 2004/084116 discloses a system for presenting and distributing medication information. According to the document, a medicament delivery device is arranged with communication mechanisms which will enable communication with a terminal device such as a cellular or a mobile phone or a PDA. A preferred communication standard is Bluetooth. The medicament delivery device is arranged with a number of sensors for monitoring and registering e.g. a dose delivery sequence. The idea is then to use the functionality of the terminal device, such as its display, its processor, its keyboard, etc. instead of providing the medicament delivery device with such features. The transfer of the functionality to the terminal device will reduce the cost of the medicament delivery device in comparison with medicament delivery devices provided with such functionality.

However, a drawback with the solution according to WO 2004/084116 is that a Bluetooth circuit, or the like wireless communication systems such as ANT or ZigBee, is used. Such circuits require a certain space in a medicament delivery device as well as a battery to power the circuit. Further, even if prices of such circuits have gone down, they are still too expensive for some applications, and in particular if the medicament delivery device is a disposable device.

Other communication technologies that might be interesting are for instance radio frequency identification (RFID) tags. If passive RFID-tags are used, then no battery is required and the tags can be made very small. One favourable solution is to produce the tags as labels or stickers that can be attached to surfaces of a device. In the technical area of medicament delivery devices, RFID has been used to some extent for identifying certain components comprised in the medicament delivery device, completed operation sequence or for collecting information regarding adherence of a medicament delivery scheme.

Regarding identification, document U.S. Pat. No. 8,355,753 discloses a medication site arranged with a medication port to which a medicament container may be releasibly attached. The neck portion of the medicament container is in one embodiment arranged with an RFID-tag with an antenna that can be connected or disconnected by a switch. When the medicament container is connected to the medication port, the switch connects the antenna and the information on the RFID-tag can be read by an RFID-reader in the medication site. The information contained in the RFID-tag may be the type of drug contained. According to another embodiment in U.S. Pat. No. 8,355,753, an RFID-tag may be arranged to be activated when medication has been delivered, thus sending information to the medication site that the delivery sequence is completed.

The drawback with the medication site according to U.S. Pat. No. 8,355,753 is that the device as such is rather complex and expensive, comprising a number of features and functions that are not a part of self-administering medicament delivery devices and certainly not for disposable medicament delivery devices.

BRIEF DESCRIPTION OF INVENTION

The aim of the present invention is to provide information from a medicament delivery device to a user regarding the status and changes of status of the medicament delivery device.

This aim is solved by a medicament delivery device and a communication system comprising the features of the independent patent claims. Preferable embodiments of the invention form the subject of the dependent patent claims.

According to a main feature of the invention, it comprises a medicament delivery device comprising a housing, which housing is arranged to accommodate a medicament container. Preferably a drive unit is operably arranged to act on the medicament container for expelling a dose of medicament. The drive unit may comprise a plunger rod that might be pushed or driven in the proximal direction of the medicament delivery device so that it acts on the medicament container. The drive unit may further comprise a drive force member such as a spring, even though the drive force member also may be a finger of a user such as with pen injectors.

The medicament delivery device may further comprise an activation unit operably connected to the drive unit for activating the drive unit. If a drive force member such as a spring is utilized, the activation unit may be elements that are capable of releasing the spring, which preferably is in a tensioned state. With a manually operated medicament delivery device, the activation unit may be a contact surface of a push button.

As mentioned above, the drive unit may comprise a plunger rod as an actuation element that is arranged movable inside the housing from an initial position prior to activation, to a displaced position after activation. In this respect, there may be other components and elements that will act as actuation elements being involved in the delivery of medicament. According to one feasible solution, the actuation element may be arranged as a generally tubular rotator that is rotatable between an initial position to a displaced position, and wherein the rotator is operably connected to a plunger rod and capable of releasing the plunger rod for expelling a dose of medicament.

According to a favourable solution, the medicament delivery device comprises at least a first NFC-chip arranged on the actuation element, where the NFC-chip may comprise specific information. Further, at least one shielding element may be arranged to the housing, such as to shield the NFC-chip from being read by an NFC-chip reader when the actuation element is either in the initial position or in the displaced position. With this solution it is possible to detect the status of the medicament delivery device by utilizing the signals from the NFC-chip when it is in a specific position allowing the NFC-chip to be read. In other positions, it is not possible to read the NFC-chip due to the shielding element.

According to on feasible solution, the actuation element may be arranged with at least two NFC-chips, wherein the at least one shielding element is arranged to shield a first NFC-chip and to allow reading of a second NFC-chip when the actuation element is in the initial position, and to shield the second NFC-chip and to allow reading of the first NFC-chip when the actuation element is in the displaced position. The NFC-chips are then preferably programmed such that they have specific information related to the position of the actuation element, and thus the status of the medicament delivery device.

For instance, the first NFC-chip may have information that informs that the medicament delivery device is unused, i.e. ready to be used for deliver a dose of medicament, wherein the second NFC-chip may contain information that the medicament delivery device has been used and may be discarded. Further information from the second NFC-chip may be that the dose delivery sequence has ended and that it is safe to remove the medicament delivery device from the dose delivery site.

According to a favourable solution, the shielding element may comprise an opening arranged such that the at least first NFC-chip is positioned in the opening when the actuation element is either in the initial position or in the displaced position. With the use of a rotator as mentioned above, the NFC-chips may be arranged on an outer circumferential surface where the shielding element is arranged coaxially outside the rotator and the NFC-chips, wherein the NFC-chips are positioned such in relation to the opening of the shielding element that the first NFC-chip is aligned with the opening in the initial position while the second NFC-chip is shielded behind the shielding element. During activation of the medicament delivery device and during the dose delivery sequence, the rotator rotates such that the second NFC-chip is aligned with the opening while the first NFC-chip is shielded behind the shielding element.

As seen in a larger context, the invention may comprise a communication system comprising a medicament delivery device provided with the above described features, wherein the communication system may comprise a smart device arranged and designed to communicate with the at least one NFC-tag for receiving specific information from the chip, wherein the at least one NFC-tag is operably connected to the medicament delivery device for obtaining information regarding the status of the medicament delivery device. This solution enables the use of a smart device such as a smart phone, a tablet computer or the like electronic devices. In this respect, it is an advantage if the smart device is arranged with functions to read NFC-chips, enabling retrieval of information from the at least one NFC-chips by the smart devices.

The smart device may then be used to obtain the information from the at least one NFC-tag, which in turn is operably connected to the medicament delivery device for obtaining information regarding changes of status of the medicament delivery device. As mentioned above, a user may be presented with information in his or her smart phone that the medicament delivery device has completed a dose delivery sequence and that it is safe to remove the medicament delivery device.

In this context, the functions of the smart device may be utilized in order to inform the user. For example the display of the smart device may be used as well as the audio functions. The smart device may give further information, such as how to discard the used medicament delivery device, give information when the next dose delivery operation is to be performed etc.

As an extension of the possibilities of communicating the information from the medicament delivery device, the smart device may be arranged with network mechanisms capable of connecting the smart device to external network and being operably capable of transmitting information to external receivers based on the specific information from the at least one NFC-tag. With this solution, the information may be transmitted to for instance a physician or other medical staff that are for example responsible for the treatment scheme of the user.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 displays a first scenario according to the invention comprising an NFC-tag and a smart device, FIG. 2 displays the use of a label comprising an NFC-tag capable of providing status information of several features and functions of a medicament delivery device, FIG. 3 displays a second scenario according to the invention with a higher level of integration between NFC-tags and smart devices, FIG. 5 is a cross-sectional view of the medicament delivery device of FIG. 4, FIG. 6 is a detailed view of a power unit comprised in the medicament delivery device of FIG. 4, FIG. 7A displays an example of the use of several NFC-tags in one medicament delivery device, FIG. 7B displays an example of the use of several NFC-tags in one medicament delivery device, FIG. 8 displays an example of physical integration of a medicament delivery device comprising NFC-tags and a smart device, FIG. 9 displays schematically an information provider system, FIG. 10 displays a first embodiment of an information providing function that may be used in the information providing system of FIG. 9, FIG. 11 displays a second embodiment of an information providing function, FIG. 12 displays an information provider system as a package for a product, and FIG. 13 displays the use of the information provider system of FIG. 12.

DETAILED DESCRIPTION OF THE INVENTION

Figure 1:
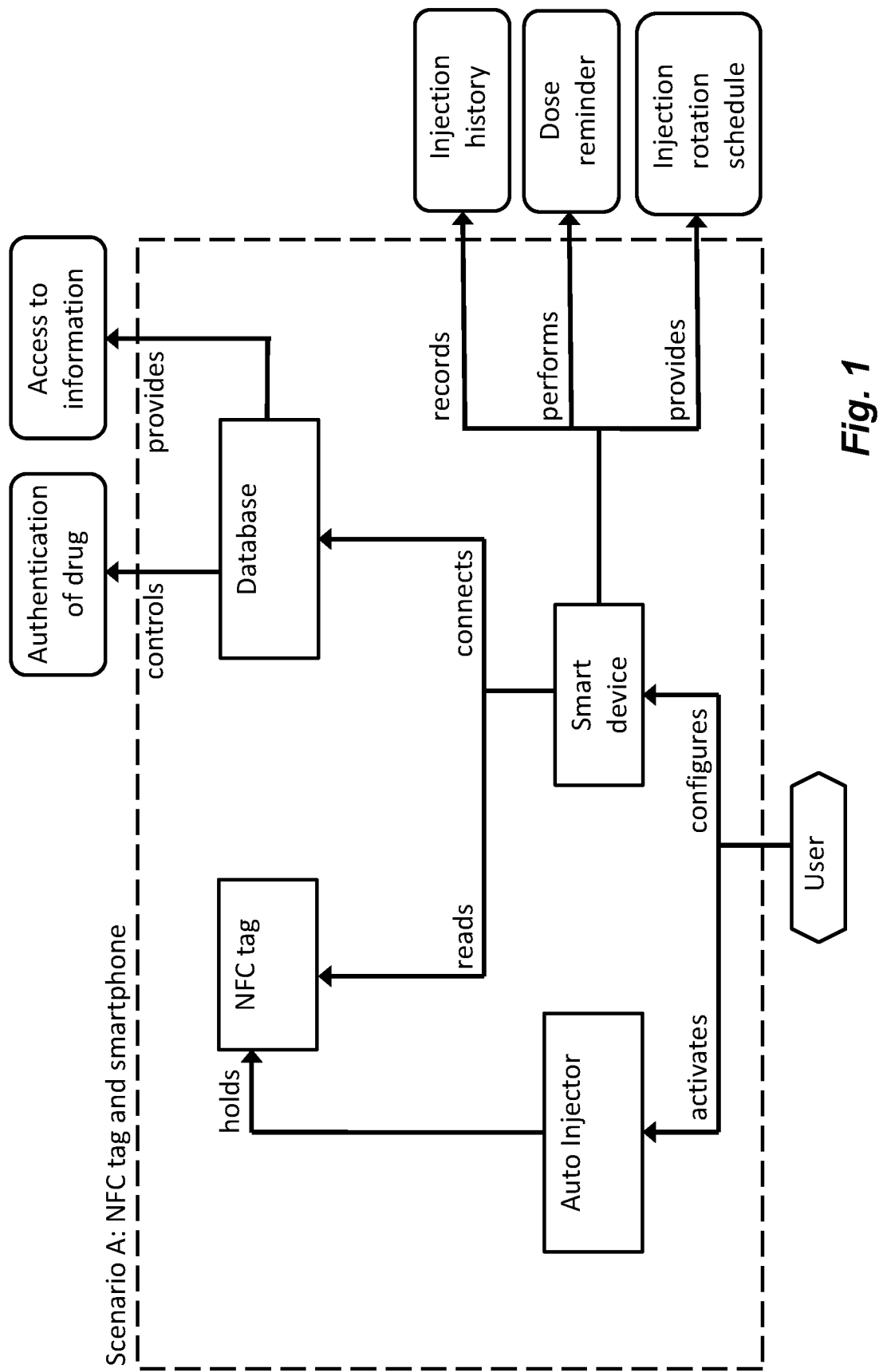

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form. The medicament delivery devices may be of either disposable type or re-usable type and may be provided with medicament containers suitably arranged for specific drugs in specific forms.

The communication system of the present application comprises the use of radio frequency identification technology, RFID. In particular, high frequency RFID provides a number of advantages regarding communication. The possibilities of using HF RFID are numerous and in particular provides the use of Near Field Communication, NFC. NFC is particularly suitable because it is a set of standards for smartphones and the like smart devices to establish radio communication. NFC is a set of short-range wireless technologies, typically requiring a distance of 10 cm or less. NFC operates at 13.56 MHz on ISO/IEC 18000-3 air interface and at rates ranging from 106 kbit/s to 424 kbit/s. NFC always involves an initiator and a target; the initiator actively generates an RF field that can power a passive target. This enables NFC targets to take very simple form factors such as tags, stickers, key fobs, or cards that do not require batteries.

In the following description of the technology used the word NFC-tag will be used. In this context it is to be understood that NFC-tag will comprise an NFC-chip connected to a circuit as well as an antenna. NFC-tag is not limited to be integrated in a patch or label, but may be a stand-alone unit, or integrated in the material used for manufacturing medicament delivery devices. Further, the NFC-tag may include further features and components that are needed for the required or desired purposes and applications as will be apparent below.

NFC tags contain data and are typically read-only, but may be rewriteable. They can be custom-encoded by their manufacturers or use the specifications provided by the NFC Forum, an industry association charged with promoting the technology and setting key standards. The tags can securely store personal data such as debit and credit card information, loyalty program data, PINs and networking contacts, among other information.

Near-field communication uses magnetic induction between two loop antennas located within each other's near field, effectively forming an air-core transformer. There are two communication modes, passive and active mode. In the passive communication mode, the initiator device provides a carrier field and the target device answers by modulating the existing field. In this mode, the target device may draw its operating power from the initiator-provided electromagnetic field, thus making the target device a transponder. In the active communication mode, both initiator and target device communicate by alternately generating their own fields. A device deactivates its RF field while it is waiting for data. In this mode, both devices typically have power supplies. As to be understood in the following description in the area of medicament delivery devices, the initiator device is a smart device as defined above, and the target device is a medicament delivery device as defined above.

Regarding medicament delivery devices, they can be arranged with NFC tags in order to perform a number of tasks. The NFC tags may be arranged as labels on an outer or inner surface of a housing of a medicament delivery device. It may also be embedded or cast into the material of the medicament delivery device.

FIG. 1 displays a first possible scenario comprising NFC tags and smart devices. In its most simple application, the NFC tags may be arranged to perform functions that do not require specific approvals from national drug regulation authorities such as the FDA in USA that the device is e.g. safe and effective. Such functions may comprise authentication of the drug that is inside the medicament delivery device. In that respect, the NFC tags may be placed on the medicament containers, for example if the medicament delivery device is a reusable device that may be used for a number of medicament containers.

Alternatively the NFC tags may be a part of the medicament delivery device, either as a label added to the device during assembly or embedded into the material when casting the device, e.g. in the housing.

The NFC tags may further provide information regarding expiry date of the drug. Alternatively, the communication with the smart device may trigger the smart device to connect to a remote database where information regarding the drug may be retrieved, such as the expiry date. The information from the database may further include if any recalls can or have affected the unique drug and/or the medicament delivery device.

The NFC tags may further include functions that, when communicating with the smart device, may start programs or applications in the smart device that provides the user with information. The programs and/or applications may be stored in the smart device but may also, or instead, be stored in external databases that are either retrieved by the smart device or run via web browsers. In that respect, the NFC tags may trigger a web browser of the smart device to activate certain URL's. These may comprise e.g. instructions for use of the medicament delivery device, where the URL may lead to a web page containing a written description of how to use the device.

In addition, or instead, the targeted web page may include a video recording, that also could include a narrator, showing and describing how to use the device. Further information that could be provided to the user is contact information to health care providers, such as e.g. telephone numbers, e-mail addresses, maps etc. Further information to a user may comprise reminders and schedules for dose delivery, such as dose delivery intervals, at what times during the day the dose should be taken etc. This dose delivery information may be manually generated in that the user or a physician enters the information into the smart device, which could be done via a calendar function. The information could also be generated electronically from prescription, wherein the information is obtained through communication with external databases via networks. The smart device could then provide the user with reminding information when it is time to take a dose of medicament, wherein the reminder could include all sorts indications such as text messages on the display of the smart device, audible signals or voice messages, vibrations, flashes, just to mention a few possibilities.

Other types of information could comprise reminders and schedules regarding using different dose delivery sites, which may be quite important when injection devices are used and wherein repeated injections on the same site may cause scars tissue, and or where the drug injected may cause irritation of the skin. These schedules could comprise visual information on the display of the smart device showing graphically where on the body the next dose should be delivered. This type of information may then be displayed in connection with the reminder of taking a dose of medicament.

The storage facilities of the smart device may further be used to store unique ID of the drug used, wherein specific information may be connected to the drug in order to build up medicament delivery history. In this respect, medicament delivery history, e.g. injection history, may comprise information regarding date and time of information read by the smart device of performed drug delivery occasions. It is in this scenario thus important that the reading of the NFC-chip is performed close after the dose has been delivered in order for the information to be as accurate as possible.

The information may further, or instead, comprise delivered dose size, if for example the medicament delivery device may be provided with mechanism for setting and delivering different dose sizes. The information may be compared by the smart device with prescribed drug delivery intervals and/or dose sizes in order to detect any deviations. Any deviations may be stored in the smart device and/or transmitted to the physician of the user. It is however to be understood, as mentioned above, that the information, written and/or visual and/or audible, may be comprised in the programs or the applications that may be stored in the smart device. The user may also be alerted by the smart device of any deviations and may possibly be given options regarding remedy of the deviations.

Figure 2:
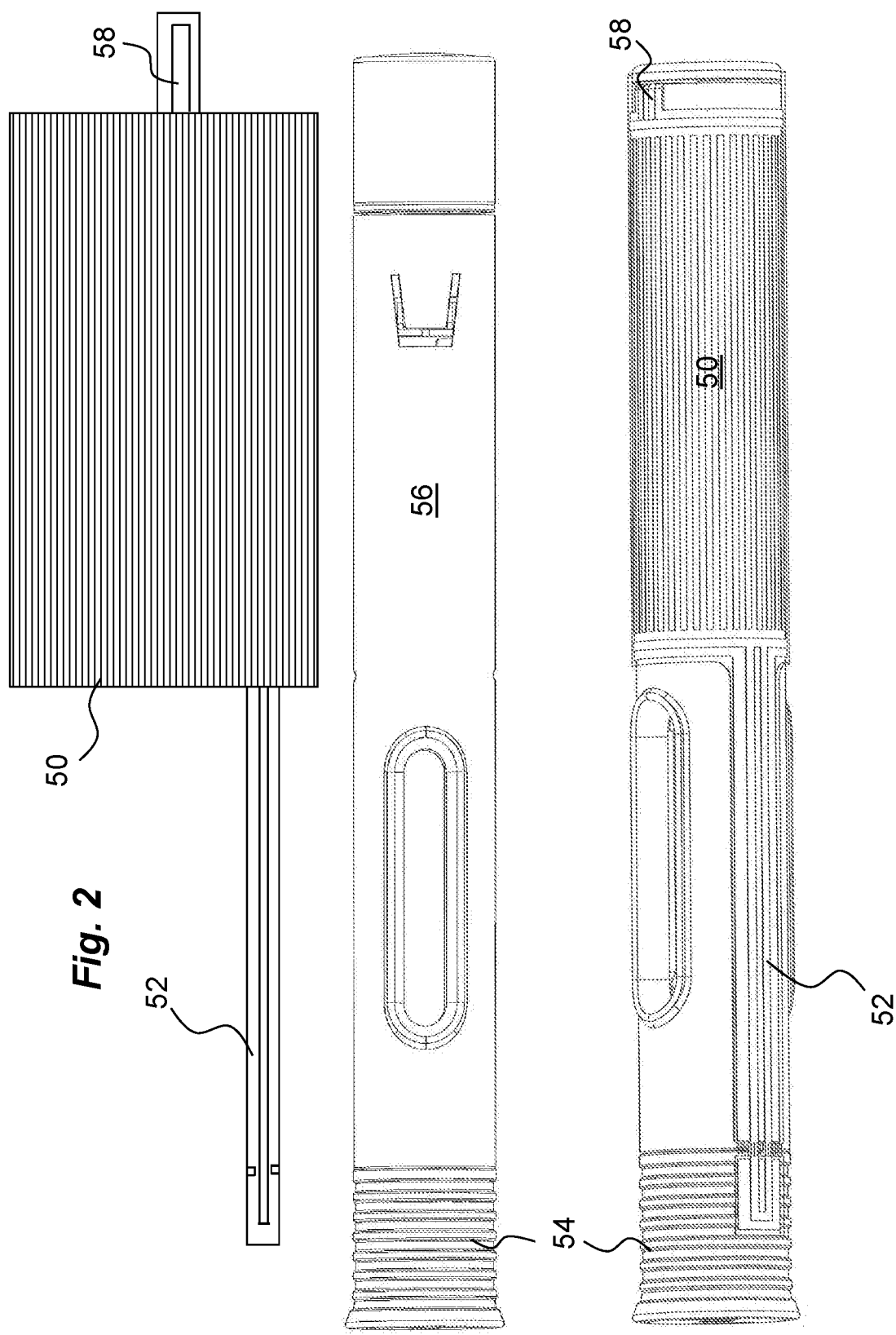

A further scenario regarding the present invention is to provide more information regarding the status of the medicament delivery device in the communication between one or more NFC chips and smart devices, thereby increasing the level of integration between the medicament delivery device and the smart device. An example of this is shown in FIG. 2. In this scenario, NFC-chips 50 are used that are capable of detecting and identifying if a certain circuit on the medicament delivery device is open or closed. This capability may be used for providing information regarding the status of the medicament delivery device.

Figure 3:
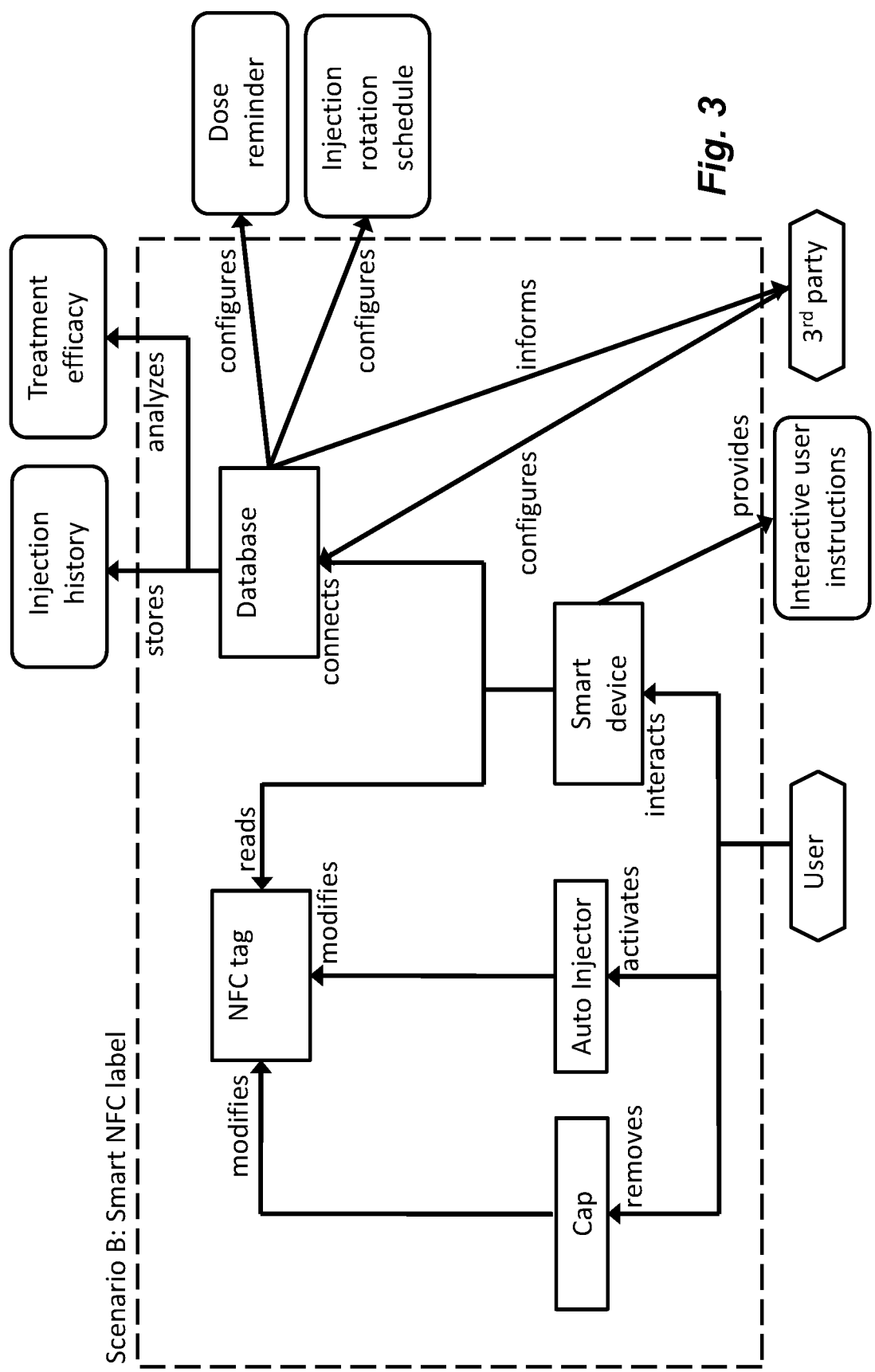

For instance circuits may be connected to a number of functions and components of the device. As an example, a circuit 52 may be connected to a protective cap 54 of the device. When a user removes the cap 54 the circuit is broken and thus closed, which may be detected by the NFC 50 and this information may be transmitted to the smart device as seen in FIG. 3. The smart device can store this information and/or transmit it to external databases, adding to the device history, which may be monitored by e.g. the physician of the user.

Circuits may thus be connected to a number of components for providing status information. Such status information may comprise end of dose delivery. It may for example be important for a user to know when an injection sequence has ended and that it is safe to remove the device from the injection site. In this case a circuit 58 may be affected by moving components at the end of dose delivery, wherein the circuit acts as a switch, e.g. from open to closed. For instance, the moving component may be a force member like a drive spring that is capable of acting in the distal direction of the medicament delivery device at the end of an injection sequence, wherein the distal action will affect the NFC circuit 58. The switch information detected by the NFC is transmitted to the smart device, wherein the smart device is arranged to indicate to the user that the device may safely be removed. Also, this information confirms that the device is used.

The circuits and switches may further be used as interactive, step by step, instructions. For example, the smart device may be provided with an instruction application showing a user in a step-wise manner how a device should be handled. When one step has been performed, whereby a certain circuit has been affected and detected by the NFC and transmitted to the smart device, an OK or positive response is provided by the smart device and displayed to the user. The instruction application then shows the subsequent handling step to be taken. In this manner, all steps affect different circuits that in turn provide the NFC chip with status information. This status information is successively transmitted to the smart device and appropriate information is displayed to the user by the instruction application.

In this context it is to be understood that there are numerous functions that can be monitored by the use of circuits connected to the NFC chips. These could include tamper evidence of the medicament delivery device, tamper evidence of trying to manipulate e.g. a label comprising an NFC attached to a medicament delivery device.

In connection with the increased integration of the medicament delivery device and the smart device, further information could be collected in order to increase the understanding of the effects of a certain treatment scheme, e.g. disease monitoring. The programs or applications that are used in the smart device in connection with the medicament delivery devices may further include questionnaires that are filled in by the user in connection with a dose delivery operation. The questionnaire may include a number of questions regarding the current status of the patient and may preferably be configurable depending on therapy, disease and user needs. The areas that might be handled may include quality of life, cognitive function, pain, fatigue, nausea, mental health, etc. The answers of the questionnaire may then be transmitted from the smart device to external databases together with information collected via the NFC-tags for processing and evaluation to find positive or negative correlations between the treatment scheme and type of medicament in relation to the perceived condition of the patient.

Figure 4:
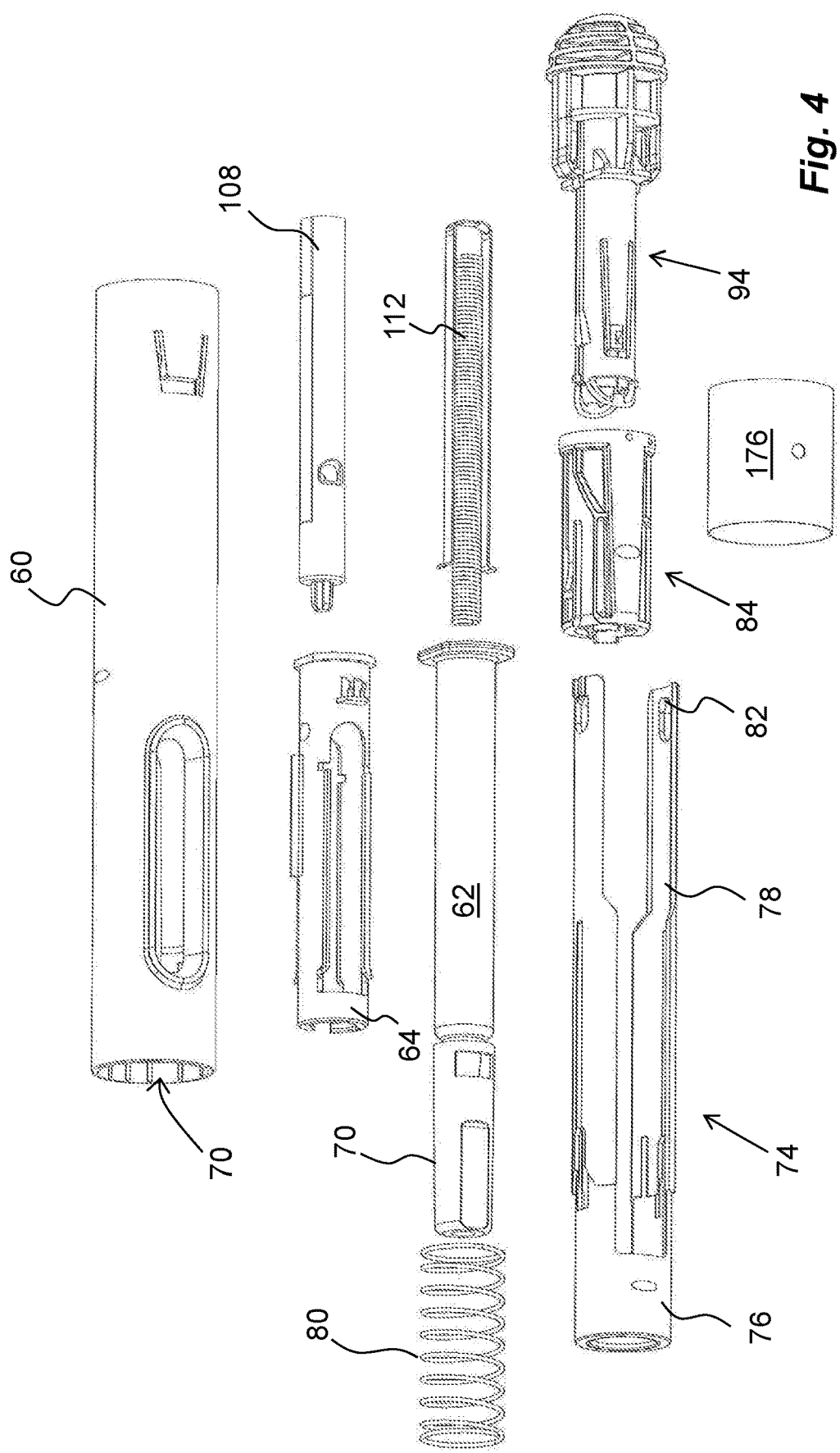
FIG. 4 shows an exploded view of a medicament delivery device that may be provided with information carrying NFC-tags.

It is to be understood that more than one NFC-tag may be used on one device, where the different NFC-chips are arranged to handle for example different states of a device. In this scenario it may be important that only one NFC-tag at the time may be read by the smart device. FIG. 4 shows a possible use of several NFC-tags in connection with a medicament delivery device.

The medicament delivery device comprises a generally tubular elongated housing 60, FIG. 4. A medicament container 62 is placed in a medicament container holder 64, which in turn is positioned in the housing 60. The medicament container 62 is arranged with a movable stopper 66, FIG. 5. The medicament container 62 has a proximal end on which a medicament delivery member 68, FIG. 5, is arranged, either made integral or connectable to the medicament container 62. The medicament delivery member 68 is preferably protected before use by a medicament delivery member shield 70 that in the embodiment shown is a so called rigid needle shield or RNS. It is however to be understood that other types of medicament delivery member shields may be used in order to obtain the desired protection of the medicament delivery member 68.

The proximal end of the housing is arranged with a central passage 72, FIG. 4, through which a generally tubular medicament delivery member guard 74 extends, FIG. 4. The medicament delivery member guard 74 comprises a proximal tubular part 76 and two distally directed arms 78 extending from the tubular part 76. A medicament delivery member guard spring 80, FIG. 4, is arranged between a distally directed circumferential wall part of the medicament delivery member guard 74 and a proximally directed surface of the housing. The arms 78 are arranged slidable along the medicament container holder 64. At the distal end of the arms 78, inwardly directed protrusions 82 are arranged, FIG. 4. The protrusions 82 are arranged to operably interact with a tubular rotator 84, FIGS. 4 and 6, of a drive unit 86.

The rotator 84 has a generally tubular shape and is arranged with guide ridges 88 that are intended to cooperate with the protrusions 82 of the medicament delivery member guard 72 as will be described, wherein some sections 88, of the guide ridges are inclined in relation to the longitudinal axis L of the device. A proximal part of the rotator 84 is further arranged with proximally directed tongues 90 adjacent the guide ridges, wherein the free ends of the tongues 90 are arranged with wedge-shaped outwardly directed protrusions 92, the function of which will be described below.

An actuator 94, FIGS. 4 and 6, is further arranged operably to the rotator 84. It comprises a first proximal tubular section 96 having a diameter slightly smaller than the inner diameter of the rotator 84. It further comprises a generally tubular second section 98 arranged to fit into and to be attached to a distal part of the housing.

The first section 96 is further arranged with proximally extending arms 100 that are arranged flexible in a generally radial direction. The free ends of the arms 100 have outwardly extending protrusions 102 that are to interact with inner surfaces of the rotator 84 as will be described. Further the free ends of the arms 100 are arranged with inwardly extending protrusions 104, which protrusions 104 are intended to interact with recesses 106 on a generally elongated plunger rod 108, FIG. 6. The protrusions 104 extend into a central passage 110 of the actuator 94, in which passage 110 the plunger rod 108 fits.

The drive unit 86 further comprises a drive spring 112, FIG. 6, that in the embodiment shown is placed inside a cavity of the hollow plunger rod 108, wherein the drive spring 112 is positioned with a proximal end thereof in contact with an end wall 114 of the plunger rod 108, FIG. 5. The distal end of the drive spring 112 is in contact with a generally U-shaped element, hereafter named activator 116, having a base 118 and two arms 120, FIG. 6. The arms 120 of the activator 114 are directed in the proximal direction along, and in contact with, the outer surface of the plunger rod 108, wherein the free ends of the arms 120 are arranged with generally radially outwardly directed ledges 122. These ledges 122 are arranged to be in contact with a proximally directed surface 124, FIG. 6, surrounding the central passage 110 of the actuator 94.

The device is intended to function as follows. When the medicament delivery device is delivered to a user, a medicament container 62 with an attached medicament delivery member shield 70 has been placed in the medicament container holder 64. The drive spring 112 has been tensioned by pushing the plunger rod 108 distally relative to the actuator 94 such that the inwardly directed protrusions 104 of the arms 100 of the actuator 94 engage the recesses 106 of the plunger rod 108, thereby holding the spring-biased plunger rod 108.

When a dose of medicament is to be delivered, the proximal end of the medicament delivery device is pressed against a dose delivery site. This causes the medicament delivery member guard 74 to move inside and relative the housing 60. This in turn causes the protrusions 82 of the medicament delivery member guard 74 to move along the guide ridges 88 of the rotator 84 such that the protrusions 82 will come in contact with the inclined guide ridge 88, which will cause the rotator 84 to turn around the longitudinal axis L of the device i.e. to rotate.

The turning/rotation of the rotator 84 will cause the outwardly directed protrusions 102 of the actuator 94 to be moved out of contact with inner surfaces of the rotator 84. The arms 100 of the actuator 94 are now free to flex outwardly, whereby the inwardly directed protrusions 104 of the arms 100 are moved out of contact with the recesses 106 of the plunger rod 108.

The plunger rod 108 is now free to move in the proximal direction due to the force of the drive spring 112, wherein the proximal end of the plunger rod 108 acts on, and moves, the stopper 66 inside the medicament container 62 in the proximal direction such that a dose of medicament is expelled through the medicament delivery member 68.

When the stopper 66 has been moved by the plunger rod 108 to almost the proximal end inside the medicament container 62, the plunger rod 108 is moved out of contact with the arms 120 of the activator 116. The arms 120 of the activator 116 are thus free to flex inwards such that the ledges 122 are moved out of contact with the surfaces 124 of the actuator 94, and due to the force of the drive spring 112 in contact with and acting on the base 118 of the activator 116, the activator 116 will be moved in the distal direction a certain distance until it hits a proximally directed end wall 126 of the distal part 98 of the actuator 94, FIG. 6, thereby causing a tactile and audible signal to the user that the dose delivery sequence has ended.

When the dose has been delivered the medicament delivery device is removed from the site. This in turn will cause the medicament delivery member guard 74 to be moved in the proximal direction by the medicament delivery member shield spring 80, to extend through the proximal end of the medicament delivery device and to cover the medicament delivery member 68. Since the rotator 84 has been rotated, the protrusions 82 of the medicament delivery member guard 74 will slide over the wedge-shaped protrusions 92 of the tongues 90 of the rotator 84 and be placed proximally thereof, thereby locking the medicament delivery member guard 74 in the extended, covering position. The device can now be discarded in a safe manner.

Figure 7A:
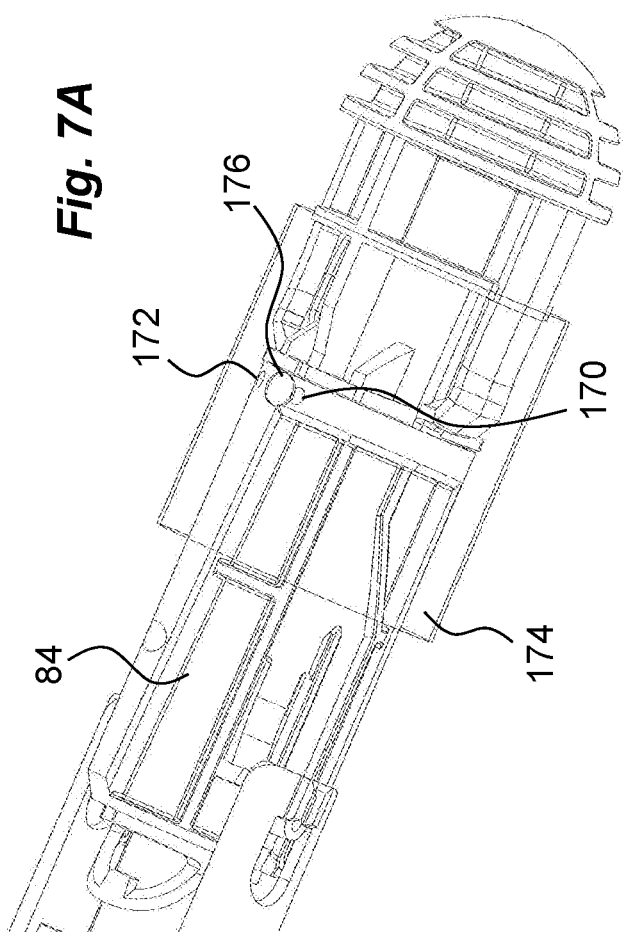
Figure 7B:
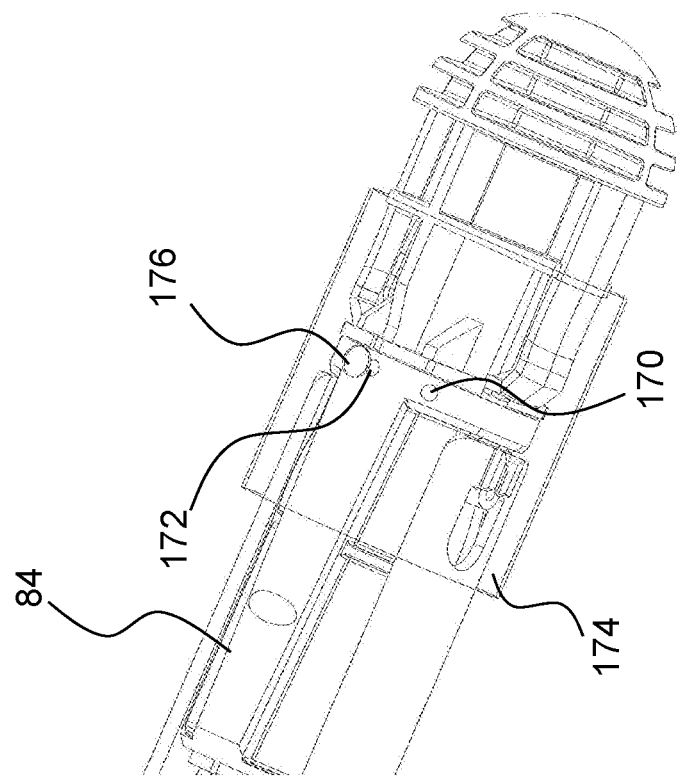

The medicament delivery device described above is arranged NFC-tags that can be used to monitor the handling of the medicament delivery device. In this shown example the rotator 84 is provided with two NFC tags 170, 172, as shown in FIG. 7A and FIG. 7B. Before dose delivery the rotator 84 has one rotational position, FIG. 7A, and after completed dose delivery, the rotator 84 has a second rotational position, FIG. 7B, as described above. This fact may be used in that each position provides information from the separate NFC-tags 170, 172. In order to ascertain that only one NFC-tag at the time can be read, a shielding element is arranged to the medicament delivery device. The shielding element may be a sheet material 174 such as a label provided with a metallic layer that is attached to the housing in the area of the NFC-tags, where the metallic layer of the sheet material 174 acts as a shield, blocking reading of the NFC-tags 170, 172. The shielding element 174 is further arranged with an opening 176, which opening 176 is positioned in relation to the NFC-tags so that a first NFC-tag 170 is aligned with the opening 176 at the first position of the rotator 84, FIG. 7A, and that a second NFC-tag 172 is aligned with the opening 176 in the second position, FIG. 7B.

Thus, in the first position, FIG. 7A, before being used, the first NFC-tag 170 may be read by a smart device, providing information that the device is unused. Further, in the second position, FIG. 7B, after use, the second NFC-tag 172 may be read by a smart device, providing information that the device has been used. It is to be understood that further NFC-tags may be used, for instance as described above in connection with removal of a protective cap. There are numerous ways in which the functions may be physically implemented. For instance, the several NFC-tags may be integrated into the material when the rotatable component is manufactured, e.g. moulded in plastic. The NFC-tags may also be attached onto the surface of the rotatable component, either glued directly or being integrated in a label that is attached to the rotatable component. Also the metallic layer may be formed in different ways. It may also be integrated in the material of the housing or be arranged as a label that is attached on the inner or outer surface of the housing.

Figure 8:
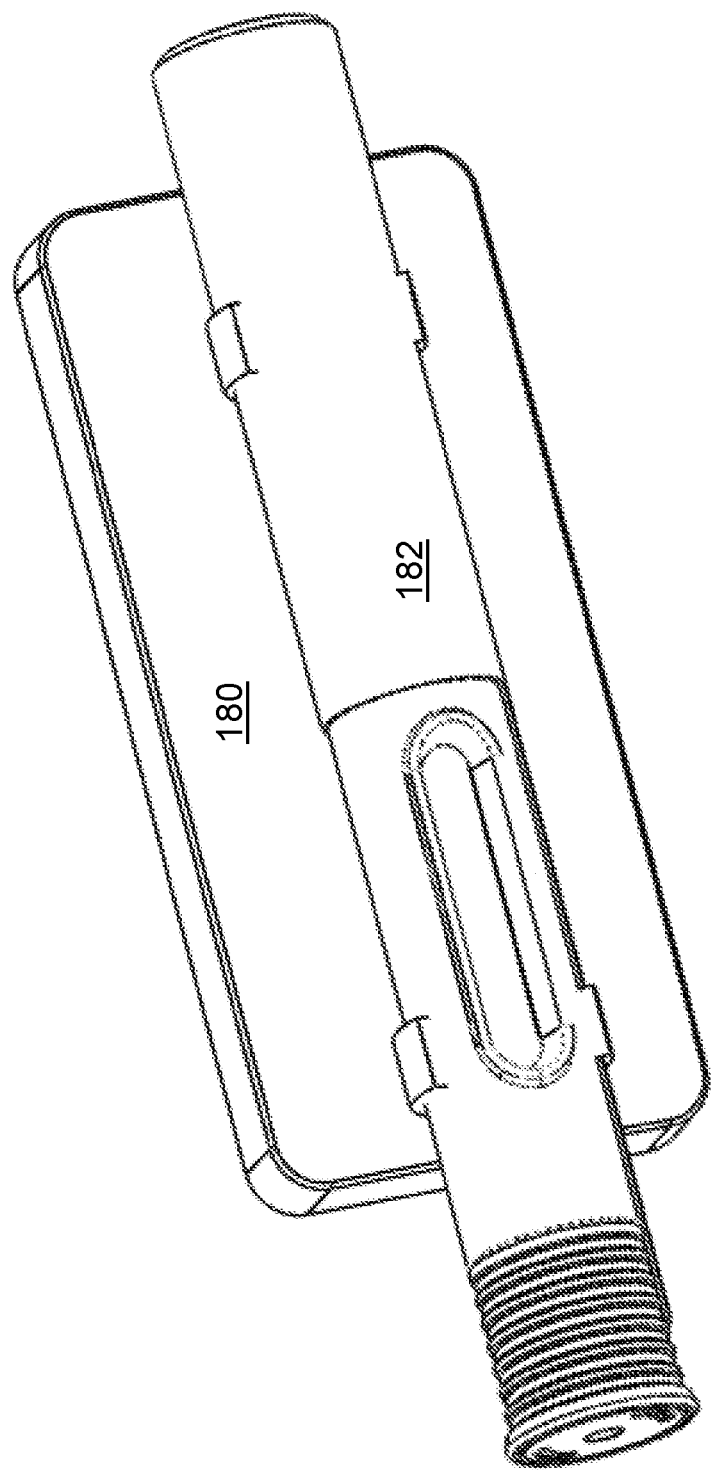

According to a further scenario of the present invention, an attachment 180 could be provided to the smart device, FIG. 8. The attachment could for example comprise a shell enclosing at least part of the smart device. This attachment enables a number of features and functions.

Preferably the attachment 180 is arranged to accommodate or hold a medicament delivery device 182. It is even feasible that the attachment and the medicament delivery device are integrated into one unit. With this feature, an even closer integration between the medicament delivery device and the smart device is obtained. This in turn provides additional advantages and features. One advantage is that the fixed connection between the medicament delivery device and the smart device enables correct reading position of the NFC-tag. Thus, the user does not have to try different distances between the medicament delivery device and the smart device in order to obtain information from the NFC-tag.

Further, if the smart device is not equipped with an NFC-reader, the attachment 180 could be provided with such an NFC-reader, thereby adding functionality to the smart device. The integration of the medicament delivery device and the smart device further provides real time interactive user instructions as well as correct injection times, dates and dose quantities because of the close connection between the medicament delivery device and the smart device because of real time reading of the NFC-tag. The injection times, dates and dose quantities can be recorded directly in the smart device for further processing or transmittal.

Many smart devices are arranged with motion sensors in three dimensions, which functionality could be used in connection with handling of the medicament delivery device. For instance, the smart device could detect how it, and thus the medicament delivery device, is being held. This may be important for some types of drugs and for some types of medicament delivery devices in that the medicament delivery device has to be held in a certain way during some steps when used. This could for example be a medicament delivery device using a so called dual chamber medicament container, where it can be important how the medicament container is held during mixing and priming. The motion sensors of the smart device could then be used to detect how the medicament delivery device is held and could inform a user on how to hold the device and alert the user if the device is not held according to instructions.

Further features of the smart device that could be used with the integrated medicament delivery device include the use of a camera that is often an integrated part of the smart device. The camera could then be used to take photographs of the content of the medicament container, which often is transparent, in order to obtain information regarding the status of the drug. For example, colouring or opacity of a drug may indicate that something adverse has happened to the drug, such as exposure to temperatures outside the prescribed range, such that the drug should not be used. The comparison of colour or opacity may be performed directly by the user in an application in the smart device, or the picture may be sent by the smart device to an external site where skilled personnel perform the comparison and alert the patient of any deficiencies of the drug and advice as to how proceed.

Regarding adherence and patient responsibility, there are features and functions of the smart device that may be utilized. Some drugs and treatment schemes are very expensive to the national healthcare authorities and a lot of responsibility is put on the users to really adhere to the treatment schemes. There has been discussions in several countries in the world that if patients do not adhere to an expensive treatment, they should be forced to pay for the continued treatment, fully or partly, the arguments being that those persons that are not interested enough in a treatment should have to pay for it. The information and drug delivery history obtained from the NFC-tags could be used to monitor the adherence.

In that respect, biometrical sensors such as fingerprint sensors, eye and/or face recognition via cameras on the smart devices mat provide proof of a user of a certain medicament delivery device, providing proof that it is the legitimate user that has activated the medicament delivery device for delivering a dose. Biometrical sensors may further be used in order to ascertain that the device cannot be accidentally, or wilfully, used by a third person.

The functionality of the NFC-tags may be further enhanced by adding a battery in that a timestamp of activation is achievable. For instance, when a switch as described above is affected, such as closing a circuit, a power circuit from the battery is thereby activated. An internal clock in the NFC-chip is thereby activated, starting to count elapsed time. This time information is then transmitted to the smart device, which could be used for a number of functions. For instance, if the clock is activated by an end of dose delivery sequence, then the smart device can easily calculate when a subsequent dose delivery is due according to dose delivery schemes contained in e.g. applications in the smart device. The smart device could then generate reminders to a user until the smart device has read information from another NFC-tag that a subsequent dose has been delivered.

Additional functionality when using a battery is that correct time information of a performed function of the medicament delivery device, such as dose delivery, is obtained regardless of when the information is read from the NFC-tag. Further, when monitoring users of a medicament delivery device during clinical trials, the feature could be used as a hidden stamp of e.g. injected dose. Used devices are then collected by the organiser of the clinical tests and actual times as read from the NFC-tags are compared with the times stated by the users in their handling notes.

One type of battery that could be used is a small one, such as a thin printed battery or a small button cell. For the above purposes there is a low capacity requirement since the battery is activated only when needed and is only used for powering the internal clock, thus there is no standby consumption. However, it is of course possible to use larger batteries in connection with NFC-tags, which enables further features and functions.

For example, if a larger battery is used, the NFC-tag could use the temperature sensor that is built into the NFC-chip. This may be an advantage because then the temperature of a medicament delivery device and/or a medicament container may be monitored and logged for instance during transport. This might be important for a number of drugs that are temperature sensitive, whereby it can be ensured that the quality of the drug has not been affected by temperature variations outside approved ranges. Also, the temperature sensor could be used to provide information when a drug has reached a target temperature for delivery. The information is then communicated to the smart device, where the latter provides handling and temperature information to the user.

When a larger battery is used, the NFC-tag could be arranged with LED's of different colour, or one LED that can change colour. The LED's are then connected to the NFC-tag such that when the temperature sensor senses a certain temperature, a certain colour is lit. When the temperature changes above or below a threshold, another colour is lit. For example, if the temperature of a drug is above or below a permissible drug delivery temperature range, then one colour is lit, e.g. a red light, indicating that the drug cannot be used yet. When then the temperature reaches the permissible range, e.g. room temperature, then the light is changed to e.g. green, indicating that the drug now may be used.

Furthermore, the temperature sensor of the NFC-chip may be used to indicate when medicament container has been emptied, i.e. a dose delivery has ended. If the NFC-tag is placed properly in relation to the medicament container, the temperature sensor may sense the temperature change that occurs between the temperature of the drug and the temperature of the empty medicament container. This significant temperature change may be used to trigger information to the smart device that the dose delivery had ended and that it is safe to remove the device. Also here, when a larger battery is arranged, there is enough power to drive for instance a light source, a vibrator and/or a summer connected to the NFC-circuit, in order to provide visual, tactile and/or audible information that a dose has been delivered.

There are further areas where NFC-tags could be used together with smart devices in medicament delivery device applications. For tutorial purposes, for instance for first time users, a sheet material could be used as an information provider, where the sheet material could be in the form of packaging of a medicament delivery device. The information provider may then be used for tutorial purposes as well as for installing specific programs and applications in a smart device, which programs and applications are to be used together with the medicament delivery device.

Figure 9:
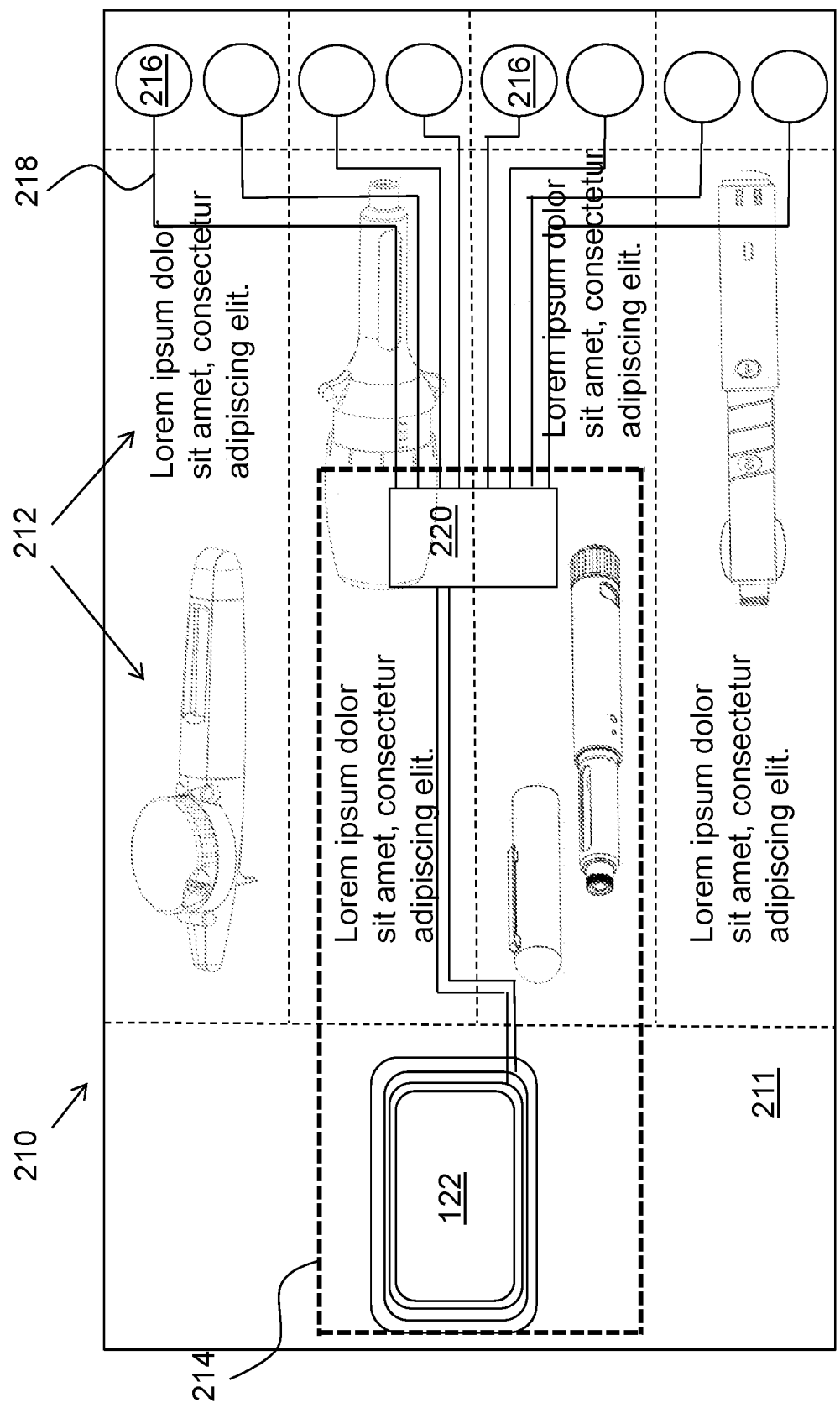

FIG. 9 shows a general example of an information provider system 210. It comprises a sheet material that preferably is foldable. The sheet material 211 may be layers of paper, cardboard, plastic or combinations thereof. The information provider system 210 may further be arranged with printed visual information 212 on one or both sides of the sheet material 211. The printed visual information 212 may comprise any suitable content that a producer of the information provider system may want to communicate. It could for example be a product presentation, where both text and figures/pictures may be shown.

In order to increase the functionality of the information provider system, an NFC-tag 214 may be included. The NFC-tag 214 could for example be arranged on a label having an adhesive on one side. The label is then attached with its adhesive side against one side of the material of the information provider system. As an alternative, the NFC-tag 214 could be embedded in the material when the material is manufactured. When the information provider system 210 is made of several layers of material, an embedded solution is especially advantageous. Further, the information provider system 210 comprises a number of specific contact areas, e.g. printed button areas that are intended to be touched or contacted by a user. Each specific contact area comprises some sort of switch 216 or activator that is affected when the specific area is touched. The switch 216 could be a simple breaker having two end leads that are brought together when the specific contact area is pressed. The switches 216 are connected to an NFC-chip 220 of the NFC-tag 214 via suitable circuitry 218. For instance the circuitry could be created by conductive ink. The NFC-tag 214 further comprises an antenna 222 that may also be embedded in the material of the packaging and connected to the NFC-chip 220. The NFC-tag 214 is arranged to cooperate with an NFC-enabled smart device 224 via the antenna 222 when in communication range.

In that respect, the information provider system 210 may comprise a marked area for placing the smart device, wherein the marked area is positioned in relation to the NFC antenna 222 such that a good connection may be established.

Figure 10:
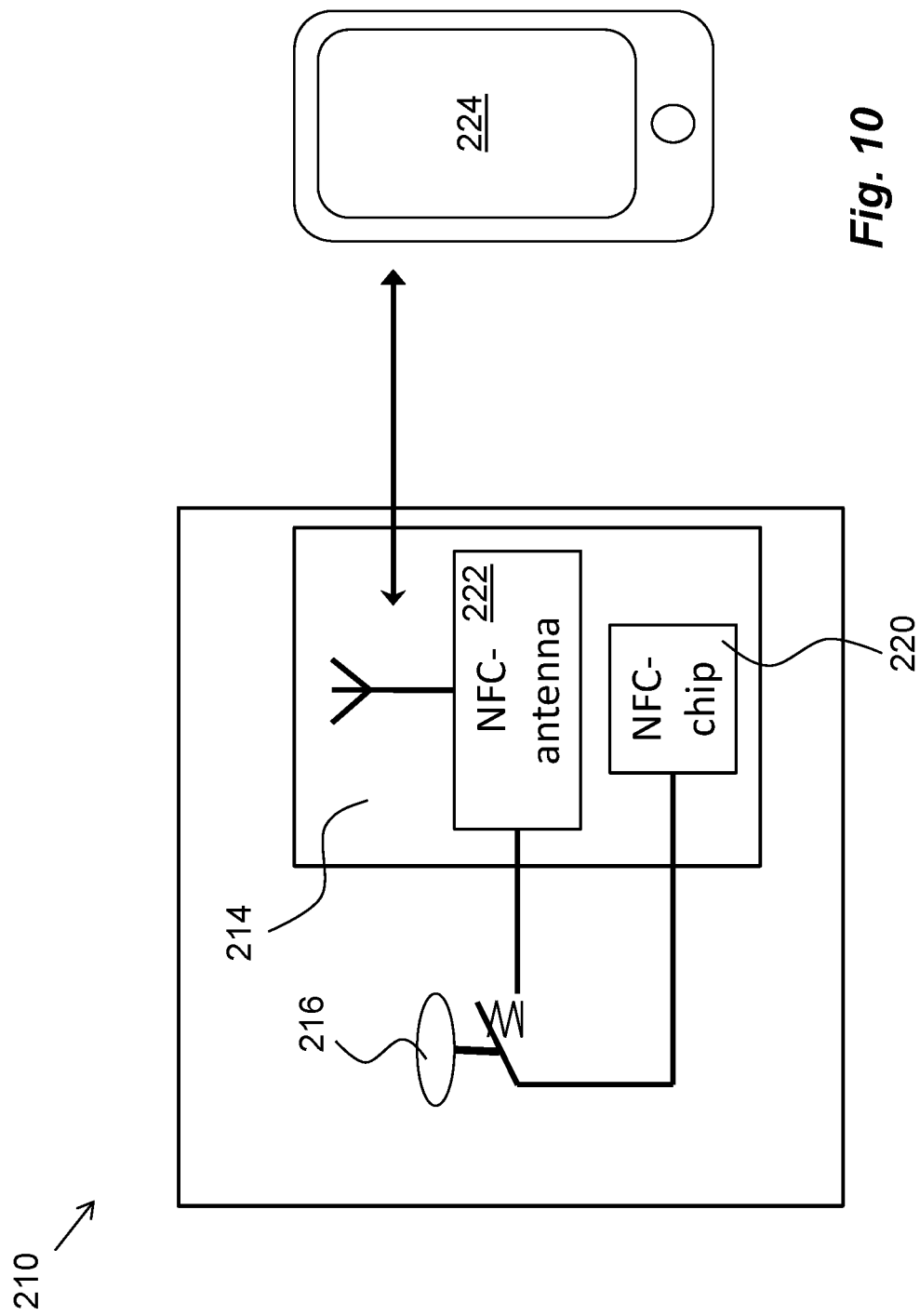

According to a solution shown schematically in FIG. 10, the information provider system 210 is arranged with one printed button area arranged as a switch 216 and intended to be touched or contacted by a user. When not activated, the switch is open. Further the switch 216 is placed between the antenna 222 and the NFC-chip 220 as seen in FIG. 10. Thus, even if a smart device 224 is placed on the marked area, the NFC-chip 220 is unaffected because the antenna 222 is disconnected. When the switch 216 is operated, the antenna 222 is connected to the NFC-chip 220, whereby the NFC-chip is energized by the connection between the antenna 222 and the smart device 224. The energizing of the NFC-chip 220 of the NFC-tag 214 causes the NFC-tag 214 to send a signal with specific information to the smart device 224 via the antenna 222. The specific information initiates a program in the smart device 224 to visually display various further information on its screen and/or to audibly present various further information via its loudspeaker. The further information is in this context related to the specific information from the NFC-tag. The further information is preferably also related to the printed visual information 112 on the information provider system 210. The further information may then be more detailed data, e.g. regarding the product that is displayed, a user manual of the product, safety and warranty documents etc.

As an example, the specific information from the NFC-tag 214 may trigger at least one step-by-step instruction program or application in the smart device, wherein the instruction is progressed each time the switch 216 is pressed. In this respect, the smart device is provided with a function that counts the number of times the switch is pressed. It is thereby feasible that when the last instruction step has been displayed on the smart device and the switch is pressed again, that the instruction re-starts with the first instruction step. The program(s) and/or application(s) may be stored in the smart device but may also be stored in external remote databases that are either retrieved by the smart device or run via web browsers. In that respect, the signal from the NFC-tag may activate the smart device to trigger a web browser to activate certain URL's. These may comprise e.g. instructions for use of the medicament delivery device, where the URL may lead to a web page containing a written description of how to use the device.

Figure 11:
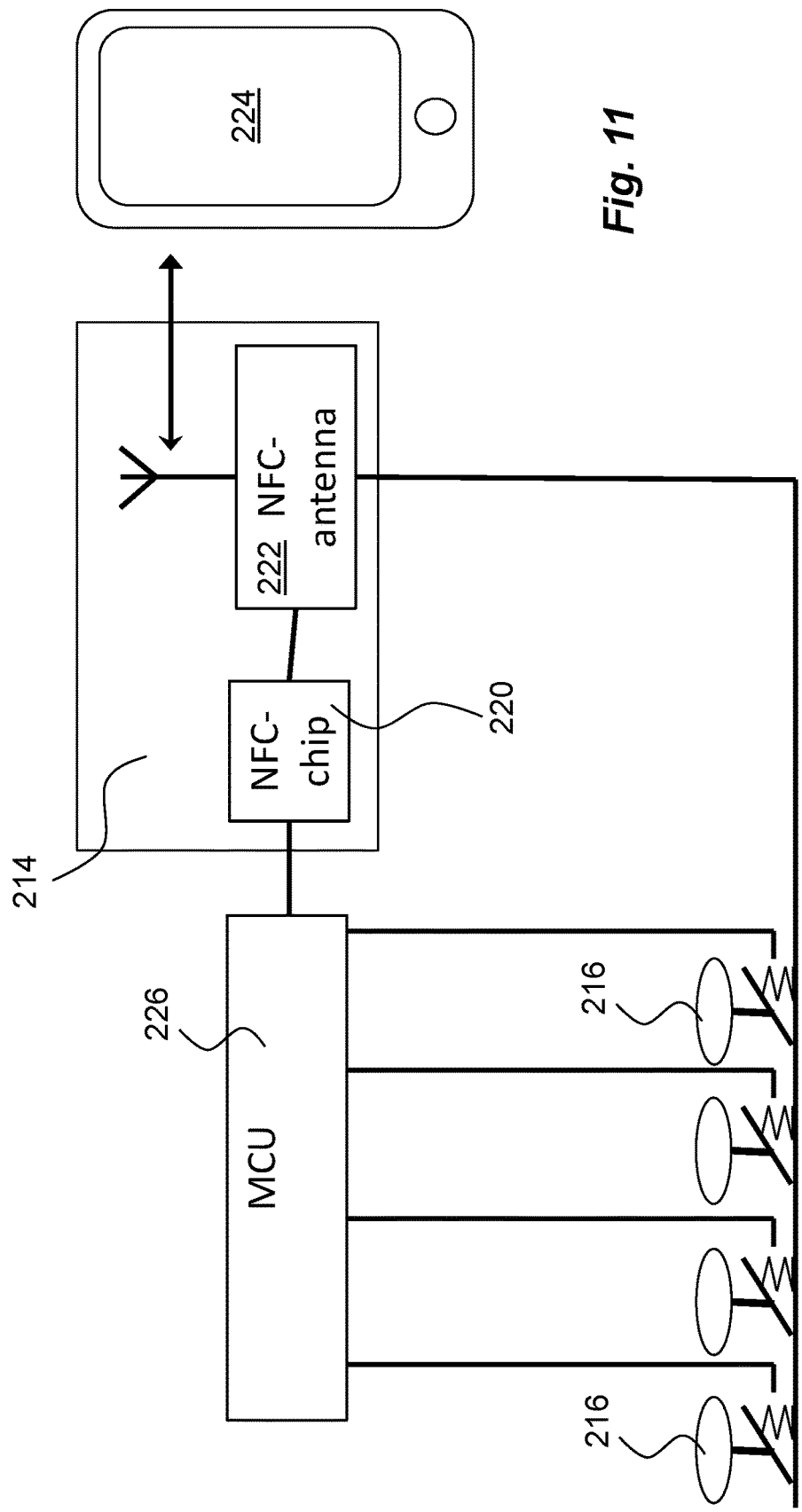

The concept can be developed to include other further information to the user by adding more switches. Preferably, a microcontroller unit 226 is included. See FIG. 11. With this solution a number of input channels may be used from a number of switches 216. The channels are connected to input gates of the micro controller. In this case the switches are not used for activating the NFC-tag 214. Instead, the NFC-tag 214 is activated when the smart device 224 is placed on the marked area. This is important because the micro-controller 226 requires power to function and the connection between the smart device 224 and the antenna 222 of the NFC-tag 214 provides energy harvesting from the smart device 224. Now the switches 216 are used as input signals to the microcontroller 226. Apart from the plurality of switches 216 providing activation of different functions, also certain predetermined combinations of active switches 216 may activate certain functions. Thus, with this solution, the possibilities are greater compared to the previously presented single-switch solution. For instance, more than one product, such as a medicament delivery device may be presented on the smart device, depending on which switch is activated. Also, different switches and/or combinations of switches may provide a choice of different languages that user instructions may be presented in. Further, switches may be used for answering quality of life questions, such as cognitive function, pain, fatigue, nausea, mental health, etc. These answers are then transmitted to the smart device via the NFC-tag, which in turn may be transmitted to dedicated receivers via suitable wireless networks that the smart device may communicate with.

A targeted web page may include a video recording of a narrator, showing and describing how to use the device. Further information that could be provided to the user is contact information to health care providers, such as telephone numbers, e-mail addresses, maps etc. Further information to a user may comprise reminders and schedules for dose delivery, such as dose delivery intervals, at what times during the day the dose should be taken etc.

The dose delivery information could be generated electronically from prescription, wherein the further information is obtained through communication with external remote databases via networks. The smart device could then provide the user with reminding information when it is time to take a dose of medicament, wherein the reminder could include all sorts of indications such as text messages on the display of the smart device, audible signals or voice messages, vibrations, flashes, just to mention a few possibilities.

Other types of further information could comprise reminders and schedules regarding using different dose delivery sites, which may be important when injection devices are used and wherein repeated injections on the same site may cause scarred tissue, and or where the drug injected may cause skin irritation. These schedules could comprise visual information on the display of the smart device showing graphically where on the body the next dose should be delivered. This type of further information may also be displayed in connection with the reminder of taking a dose of medicament.

Figure 12:
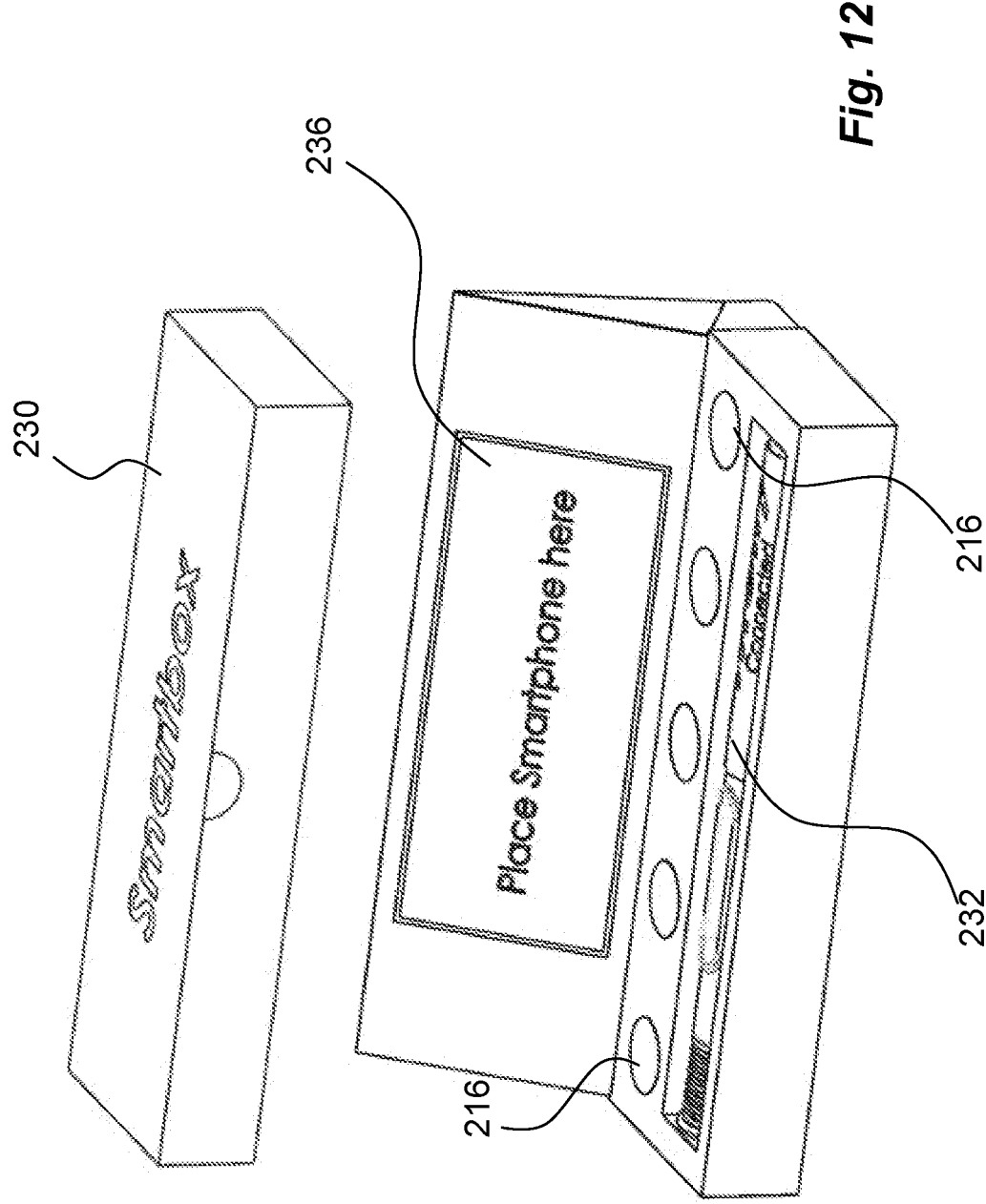
Figure 13:
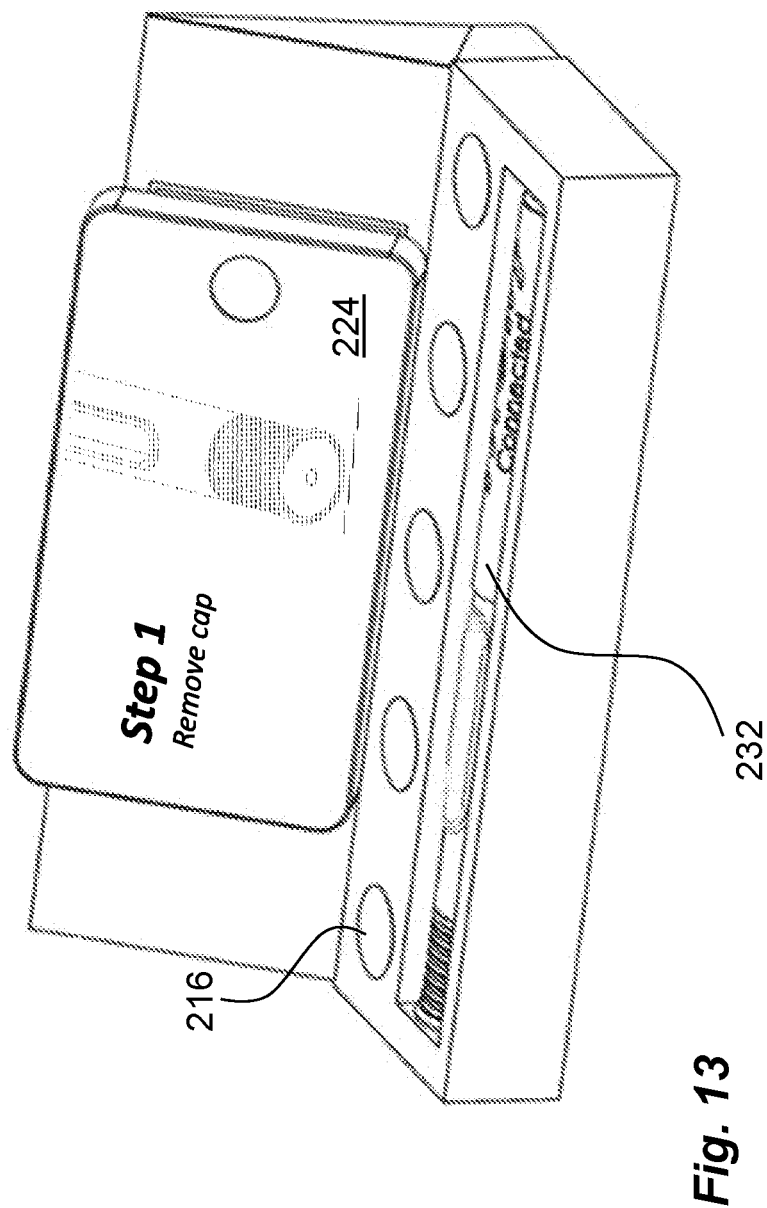

FIGS. 12 and 13 show the information provider system as a packaging 230 for a product 332, such as a medicament delivery device. In this context, the packaging of the medicament delivery device is arranged with an NFC-chip and with suitable circuitry as described above. The NFC-chip and the circuitry are preferably embedded in the packaging. A number of specific contact areas, e.g. printed button areas, that are intended to be touched or contacted by a user may be provided on the packaging, FIG. 12. Each specific contact area comprises a switch 216 under which the circuitry is placed so that touching or pressing the printed button areas will affect the switch 216 and thereby the circuitry so as to activate the NFC-chip to provide certain information. The packaging may further comprise a marked area 236 for placing the smart device 124, wherein the marked area is positioned in relation to the NFC antenna such that a good connection may be established.

When a smart device 224 is placed in the marked area of the packaging, the NFC-chip is energized by the smart device, FIG. 13. This could in turn cause an application to be installed in the smart device and started. Then, depending on which printed button area is pressed on the packaging, different further information is provided through the smart device. The further information could for instance include step-by-step instructions for use, and that could be displayed sequentially when pressing the printed button areas.

In addition to the medicament delivery devices described above, there might be further devices available to a user, or further functional features of the medicament delivery device, that could add to the functionality. For instance, additional sensors may be employed for measuring hard facts regarding the patient, where the information from the additional sensors are added to the patient history both regarding dose delivery adherence as well as health reports as established by questionnaires as mentioned above. The hard facts measured may come from blood samples, monitored heart rate, blood pressure measurements, saliva samples, just to mention a few.

It is to be understood that the embodiments described above and shown in the drawings are to be regarded only as non-limiting examples of the invention and that it may be modified in many ways within the scope of the patent protection.

The invention claimed is:

1. A medicament delivery device comprising:
a housing arranged to accommodate a medicament container;
a drive unit operably arranged to act on the medicament container for expelling a dose of medicament, the drive unit comprising an actuation element movably arranged inside the housing from an initial position prior to activation to a displaced position after activation;
an activation unit operably connected to the drive unit for activating the drive unit;
a near-field communication chip (NFC-chip) comprising information indicative of a status of the medicament delivery device; and
a shielding element arranged to shield the NFC-chip when the actuation element is in the initial position and to allow reading of the NFC-chip when the actuation element is in the displaced position.

2. The medicament delivery device of claim 1, wherein the shielding element comprises an opening arranged such that the NFC-chip is aligned with the opening when the actuation element is in the displaced position.

3. The medicament delivery device of claim 2, wherein the actuation element is configured to rotate from the initial position to the displaced position.

4. The medicament delivery device of claim 3, wherein the NFC-chip is arranged on the actuation element.

5. The medicament delivery device of claim 4, wherein the actuation element comprises a tubular rotator.

6. The medicament delivery device of claim 5, wherein the activation unit is operably coupled to the tubular rotator.

7. The medicament delivery device of claim 1, further comprising an additional NFC-chip, wherein the shielding element is arranged to allow reading of the additional NFC-chip when the actuation element is in the initial position.

8. The medicament delivery device of claim 7, wherein the additional NFC-chip is arranged on the actuation element.

9. The medicament delivery device of claim 8, wherein the actuation element is configured to rotate from the initial position to the displaced position.

10. The medicament delivery device of claim 9, wherein the NFC-chip is arranged on the actuation element.

11. The medicament delivery device of claim 1, wherein the shielding element comprises a sheet material attached to the housing.

12. A communication system comprising:
a medicament delivery device comprising:
  a housing arranged to accommodate a medicament container,
  a drive unit operably arranged to act on the medicament container for expelling a dose of medicament, the drive unit comprising an actuation element movably arranged inside the housing from an initial position prior to activation to a displaced position after activation,
  an activation unit operably connected to the drive unit for activating the drive unit,
  a near-field communication chip (NFC-chip) comprising information indicative of a status of the medicament delivery device, and
  a shielding element arranged to shield the NFC-chip when the actuation element is in the initial position and to allow reading of the NFC-chip when the actuation element is in the displaced position; and
a smart device arranged and designed to communicate with the NFC-chip for receiving the information from the NFC-chip.

13. The communication system of claim 12, wherein the smart device comprises a display configured to display information related to the information from the NFC-chip.

14. The communication system of claim 13, wherein the shielding element comprises an opening arranged such that the NFC-chip is aligned with the opening when the actuation element is in the displaced position.

15. The communication system of claim 14, wherein the actuation element is configured to rotate from the initial position to the displaced position.

16. The communication system of claim 15, wherein the NFC-chip is arranged on the actuation element.

17. The communication system of claim 16, wherein the actuation element comprises a tubular rotator.

18. The communication system of claim 17, wherein the activation unit is operably coupled to the tubular rotator.

19. A medicament delivery device comprising:
a housing arranged to accommodate a medicament container;
a drive unit operably arranged to act on the medicament container for expelling a dose of medicament, the drive unit comprising an actuation element movably arranged inside the housing from an initial position prior to activation to a displaced position after activation;
an activation unit operably connected to the drive unit for activating the drive unit;
a first near-field communication chip (NFC-chip) comprising first information;
a second NFC-chip comprising second information; and
a shielding element, wherein the shielding element is arranged to shield the first NFC-chip and to allow reading of the second NFC-chip when the actuation element is in the initial position, and wherein the shielding element is arranged to allow reading of the first NFC-chip when the actuation element is in the displaced position.

20. The medicament delivery device of claim 19, wherein the shielding element comprises an opening arranged such that the first NFC-chip is aligned with the opening when the actuation element is in the displaced position.

* * * * *